United States Patent [19]

Saca

[11] Patent Number: 5,658,246
[45] Date of Patent: Aug. 19, 1997

[54] PROTECTIVE GARMENT FOR THE HIP

[76] Inventor: Ricardo E. Saca, 1527 Parker Canyon Rd., Walnut, Calif. 91789

[21] Appl. No.: 413,412

[22] Filed: Mar. 30, 1995

[51] Int. Cl.$^6$ ................................................ A61F 5/00
[52] U.S. Cl. ................................ 602/61; 2/455; 602/62
[58] Field of Search ........................ 2/2, 238, 22, 23, 2/94, 227, 231, 267; 602/61, 60, 62, 63

[56] References Cited

U.S. PATENT DOCUMENTS

| | | |
|---|---|---|
| 3,823,711 | 7/1974 | Hatton . |
| 4,325,148 | 4/1982 | Livenois .................................. 2/2 |
| 4,558,470 | 12/1985 | Mitchell et al. ..................... 2/414 |
| 4,566,137 | 1/1986 | Gooding ............................... 2/413 |
| 4,567,887 | 2/1986 | Couch, Jr. . |
| 4,641,641 | 2/1987 | Strock . |
| 4,737,994 | 4/1988 | Galton ..................................... 2/2 |
| 4,884,295 | 12/1989 | Cox .......................................... 2/2 |
| 5,123,407 | 6/1992 | Dewhurst ............................... 602/2 |
| 5,161,257 | 11/1992 | Arensdorf et al. ..................... 2/2 |
| 5,235,703 | 8/1993 | Maynard ................................. 2/2 |
| 5,277,954 | 1/1994 | Carpenter et al. ................... 428/71 |

*Primary Examiner*—Richard J. Apley
*Assistant Examiner*—Kim Lee
*Attorney, Agent, or Firm*—David A. Farah; Sheldon & Mak, Inc.

[57] ABSTRACT

A protective garment for the hip, including the hip joint, that comprises a pair of loose fitting or form-fitting shorts having an upper right lateral section, a lower right lateral section, an upper left lateral section, a lower left lateral section and a lower back section. The garment fruther comprises protective padding in combination with one or more of these section. The padding in combination with the upper right lateral section is separated from the padding in combination with the lower right lateral section by a first gap, and the padding in combination with the upper left lateral section is separated from the padding in combination with the lower left lateral section by a second gap. The first and second gaps comprise substantially unpadded flexible material thereby allowing substantially unhindered flexion and abduction of the hip joint. The padding can be compartmentalized or noncompartmentalized and can be in a variety of configurations.

12 Claims, 4 Drawing Sheets

PROTECTIVE GARMENT FOR THE HIP

BACKGROUND

Hip fractures are a major cause of morbidity in the United States. The combination of decreased bone density and conditions affecting stability during ambulation make the elderly particularly susceptible to hip fractures.

There are several strategies for decreasing the incidence of hip fractures in the elderly. One strategy is to increase bone density through diet, exercise and the administration of exogenous substances such as estrogen. Another strategy is to increase the safety of the home and work place.

Further, there are a number of inventions which attempt to protect the hip through structures which absorb or disperse energy transmitted to the hip during a fall. These inventions have met with limited success, partly because they have poor acceptance among the elderly. Their poor acceptance is due to a number of factors, including difficultly putting on and removing the inventions and inadequate comfort for long-term wear.

Thus, there remains a need for a garment which protects the hip and is acceptable for use by the elderly. Ideally, the garment would be easy to put on and to remove by a person of advanced age. Also, the garment should be comfortable to wear for an extended period. For example, the garment would be lightweight by having padding in the areas needed to protect the hip, while avoiding extraneous padding such as would be present in garments designed for other uses. Further, the garment should be substantially permeable to water vapor so as not to create a problem with skin breakdown underneath. It would, therefore, be advantageous to have a protective garment for the hip having these features.

SUMMARY

The present invention is directed to a protective garment for the hip, including the hip joint, that satisfies these needs. According to one embodiment of the present invention, there is provided a protective garment which comprises a pair of shorts extending from a waist opening superiorly to two leg openings inferiorly. The garment has a front section anteriorly, an upper right lateral section rightward laterally adjacent to the front section, a lower right lateral section inferiorly adjacent to the upper right lateral section, an upper left lateral section leftward laterally adjacent to the front section and a lower left lateral section inferiorly adjacent to the upper left lateral section. The garment further comprises a lower right medial section medially adjacent the lower right lateral section and inferiorly adjacent the front section, a lower left medial section medially adjacent the lower left lateral section and inferiorly adjacent the front section, an upper back section posteriorly adjacent and between the upper right lateral and upper left lateral sections and a lower back section inferiorly adjacent the upper back section and posteriorly adjacent and between the upper right lateral and upper left lateral sections.

Still further, the garment comprises protective padding suitable for absorbing or dispersing energy transmitted to the hip during a fall. The padding is in combination with the upper right lateral section, the lower right lateral section, the upper left lateral section and the lower left lateral section. Further, the padding in combination with the upper right lateral section is separated from the padding in combination with the lower right lateral section by a first gap, and the padding in combination with the upper left lateral section is separated from the padding in combination with the lower left lateral section by a second gap. The first and second gap comprise substantially unpadded flexible material thereby allowing substantially unhindered flexion and abduction of the hip joint. The protective garment can be either loose fitting or can be substantially form fitting.

According to another embodiment of the present invention, there is provided a protective garment as described above with the front section, upper back section, lower right medial section and lower left medial section of the protective garment being substantially devoid of protective padding. The protective garment can further comprise protective padding in combination with the lower back section.

The padding of the protective garment according to the present invention can be compartmentalized or noncompartmentalized, or the padding in combination with at least one section can be compartmentalized while the padding in combination with at least one additional section can be noncompartmentalized. Further, the padding in at least one section can be configured in a pattern selected from the group consisting of a series of diagonally oriented compartments, a series of circularly concentric oriented compartments, a series of ovally concentric oriented compartments, a series of triangularly concentric oriented compartments, a series of rectangularly concentric oriented compartments, a series of U-shaped concentrically oriented compartments, a series of waffle-like compartments and a combination of the foregoing patterns.

In another embodiment of the present invention, there is provided a protective garment for a person's hip joint and hip comprising a pair of shorts extending from a waist opening superiorly to two leg openings inferiorly. The garment has a front section anteriorly, an upper right lateral section rightward laterally adjacent to the front section, a lower right lateral section inferiorly adjacent to the upper right lateral section, an upper left lateral section leftward laterally adjacent to the front section and a lower left lateral section inferiorly adjacent to the upper left lateral section. The garment further has a lower right medial section medially adjacent the lower right lateral section and inferiorly adjacent the front section, a lower left medial section medially adjacent the lower left lateral section and inferiorly adjacent the front section, an upper back section posteriorly adjacent and between the upper right lateral and upper left lateral sections and a lower back section inferiorly adjacent the upper back section and posteriorly adjacent and between the upper right lateral and upper left lateral sections.

The garment further has protective padding suitable for absorbing or dispersing energy transmitted to the hip during a fall. The padding is in combination with the upper right lateral section and the upper left lateral section, while the garment is substantially devoid of padding in combination with the front section, the lower right medial section, the lower left medial section and the upper back section. The protective garment can further comprise protective padding in combination with the lower right lateral section and the lower left lateral section and the padding in combination with the upper right lateral section can be separated from the padding in combination with the lower right lateral section by a first gap, while the padding in combination with the upper left lateral section is separated from the padding in combination with the lower left lateral section by a second gap. The first and second gap comprise substantially unpadded flexible material allowing substantially unhindered flexion and abduction of the hip joint.

FIGURES

These features, aspects and advantages of the present invention will become better understood with regard to the following description, appended claims in the accompanying figures where:

DESCRIPTION

In one embodiment, the present invention is a garment designed to protect the hip from injury and designed to be acceptable to the elderly for routine wear. As used herein, "hip" refers to the proximal portion of the femur and lateral portions of the pelvic bones, including the greater trochanter, the hip joint (the articulation between the head of the femur and acetabulum), those portions of the ischium and ilium adjacent to the hip joint, and to the soft tissues adjacent these structures. As used herein, "padding" refers to an aggregate of material which has substantial energy absorbing or energy dispersing properties.

Figure 1:
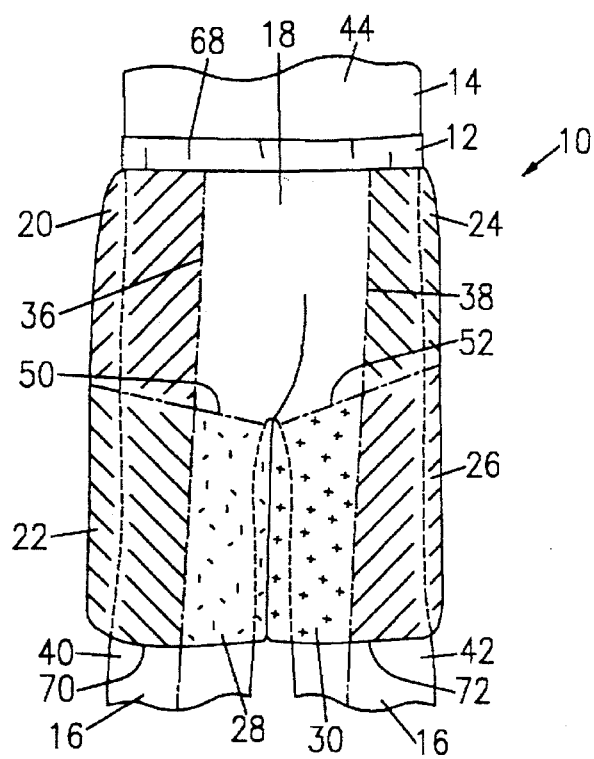
FIG. 1 is a front perspective view of a protective garment according to one embodiment of the present invention but without protective padding, showing the location of various sections of the garment.
Figure 2:
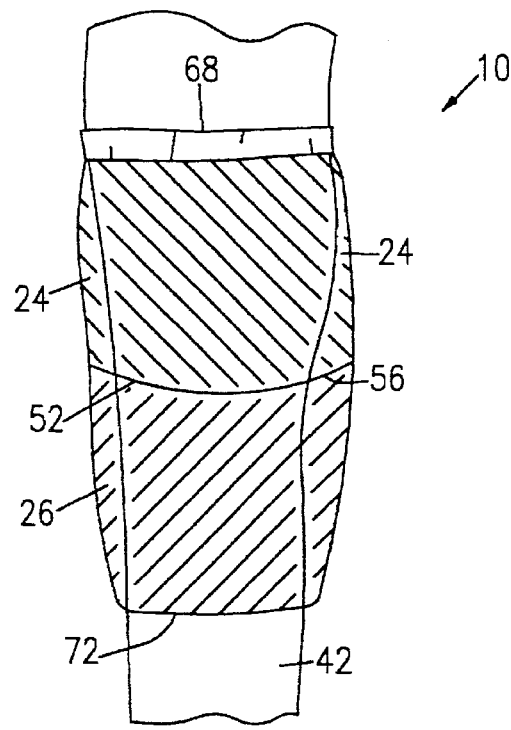
FIG. 2 is a left lateral view of the garment shown in FIG. 1 showing the location of various sections of the garment.
Figure 3:
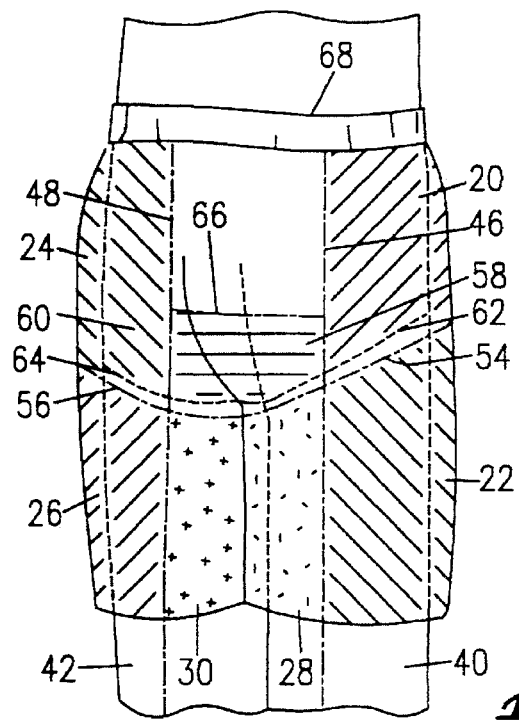
FIG. 3 is a back perspective view of the garment shown in FIG. 1 showing the location of various sections of the garment.

Referring now to FIGS. 1-3, there are illustrated a front perspective view, left lateral view and back perspective view, respectively, of a protective garment 10 according to one embodiment of the present invention but without protective padding, in order to show the location of various sections of the garment. The outline of the garment is shown by solid lines. The outline of the wearer's body covered by the garment is shown by the regular dashed lines.

As can be seen, the garment 10 resembles a pair of boxer shorts and includes a waistband 12. When worn, the garment 10 is designed to be relatively loose fitting over the area extending from the wearer's waist 14 to the upper portions of the wearer's lower extremities 16.

The protective garment 10 can comprise any of a variety of natural or synthetic materials, such as cotton, or a blend of natural or synthetic materials, as would be understood by those with skill in the art with reference to the disclosure herein. Preferably, the material is light-weight, washable, and substantially permeable to water vapor so that moisture can evaporate from the skin therethrough. The light-weight and moisture permeability advantageously increases the acceptability of the protective garment 10 for long-term wear.

The waistband 12 can be any of a variety of materials and configurations which allow it to support the garment 10 when worn as would be understood by those with skill in the art. For example, the waistband 12 can have reinforcing elastic material and can be either one piece or can open in one or more places to allow the garment 10 to be put on more easily.

Referring still to FIGS. 1-3, the garment 10 is divided into various sections in order to conveniently show the location of padding incorporated into the garment 10. These include a front section 18, an upper right lateral section 20, a lower right lateral section 22, an upper left lateral section 24, a lower left lateral section 26, a lower right medial section 28, a lower left medial section 30, an upper back section 32 and a lower back section 34.

Section boundaries are specified for convenience with the garment 10 in a position as if being worn with the wearer standing upright, as shown in FIGS. 1-3. In order to more clearly demonstrate the sections of the garment 10, reference is made herein to section boundary lines shown in the Figures as a series of alternating dots and dashes. The first two boundary lines 36 and 38 approximately bisect the right lower extremity 40 and left lower extremity 42 anteriorly, respectively, and ascend towards the abdomen 44. Next, boundary lines 46 and 48 approximately bisect the right lower extremity 40 and left lower extremity 42 posteriorly, respectively, and ascend towards the abdomen 44.

Further, boundary lines 50 and 52 divide the pelvic region anteriorly from the right lower extremity 40 and left lower extremity 42, respectively, approximately corresponding to the right inguinal fold and left inguinal fold (not shown), respectively. Lines 54 and 56 divide the right gluteal muscle mass 58 posteriorly from the right lower extremity 40 and left gluteal muscle mass 60 from the left lower extremity 42, respectively, approximately corresponding to the inferior border of the right gluteal muscle mass 62 and the inferior border of the left gluteal muscle mass 64. Finally, a boundary line 66 divides the garment 10 posteriorly approximately bisecting the right gluteal muscle mass 58 and left gluteal muscle mass 60 horizontally.

The approximate section boundaries of the garment 10 can now be appreciated with reference to the following descriptions in view of the boundary lines. A front section 18 (shown without cross-hatching) anteriorly extends superiorly to a position adjacent or near the waist opening 68, and laterally to the lines 46 and 48 and inferiorly to the lines 50 and 52.

The upper right lateral section 20 (shown with diagonal cross-hatching up to the right) extends superiorly to a position adjacent or near the waist opening 68, anteriorly to the line 36, posteriorly to the line 46 and inferiorly to the lines 50 and 54. The upper left lateral section 24 (shown with diagonal cross-hatching up to the left) extends superiorly to a position adjacent or near the waist opening 68, anteriorly to the line 38, posteriorly to the line 48 and inferiorly to the lines 52 and 56.

The lower right lateral section 22 (shown with diagonal cross-hatching up to the left) extends superiorly to the lines 50 and 54, anteriorly to the line 36, posteriorly to the line 46 and inferiorly to the right leg opening 70. The lower left lateral section 26 (shown with diagonal cross-hatching up to the left) extends superiorly to the lines 52 and 56, anteriorly to the line 38, posteriorly to the line 46 and inferiorly to the left leg opening 72.

The lower right medial section 28 (shown with a speckled pattern) extends superiorly to the lines 50 and 54, anteriorly to the line 36, posteriorly to the line 46 and inferiorly to the right leg opening 70. The lower left medial section 30 (shown with a cross pattern) extends superiorly to the lines 52 and 56, anteriorly to the lines 38, posteriorly to the line 48 and inferiorly to the left leg opening 72.

The upper back section 32 (shown without cross-hatching) extends superiorly to a position adjacent or near the waist opening 68, inferiorly to the line 66, and laterally to the lines 46 and 48. The lower back section 34 (shown with horizontal cross-hatching) extends superiorly to the line 66, laterally to the lines 46 and 48 and inferiorly to the lines 54 and 56.

According to one aspect of the present invention, padding is provided in combination with certain sections of the garment 10. The padding can comprise any suitable material, both natural, synthetic or a combination of natural and synthetic materials which have properties suitable for absorbing or dispersing a significant amount of energy such as would be delivered to the hip during a fall from a standing position onto a hard surface. In one preferred embodiment, the padding comprises cotton. In another preferred embodiment, the padding comprises foam rubber.

Within each section, the padding can be incorporated into a variety of configurations. For example, the padding can be in one piece, that is noncompartmentalized, or can be compartmentalized. When noncompartmentalized, the padding can be in any of a variety of shapes, including round, oval, triangular, rectangular, trapezoidal or other configurations. When compartmentalized, the padding can be separated into a series of horizontally oriented compartments, a series of vertically oriented compartments, a series of diagonally oriented compartments, a series of circularly, oval, triangular, rectangular or U-shaped concentrically compartments or a combination of the foregoing or other configurations such as a waffle-like configuration.

The compartments can be formed by any suitable means. For example, the padding could be placed between two or more layers of material and the material sewn together as necessary to compartmentalize the padding. Alternately, a suitable adhesive or other means can be used to join the material between the padding in order to create the compartment.

Whether compartmentalized or not compartmentalized, padding can be attached to the garment 10 in a manner which is intended to be separated from the garment 10 by the wearer or can be attached to the garment 10 in a manner which is not intended to be separated from the garment 10 by the wearer. For example, with respect to the former, padding can be sewn on to the garment 10 or can be attached by a suitable adhesive. With respect to the latter, pockets of material can be incorporated into the various sections having padding and the padding can be inserted into the pockets as needed.

Having padding which can be removed from the rest of the garment 10 is advantageous for several reasons. First, the garment 10 can be used as an article of underwear and the padding only inserted when the wearer is at particular risk for falling. Second, the padding can be removed for easier cleaning of the garment 10. Third, padding of a different material or different amount can be inserted to adapt the garment 10 to the particular needs of the wearer.

Figure 4:
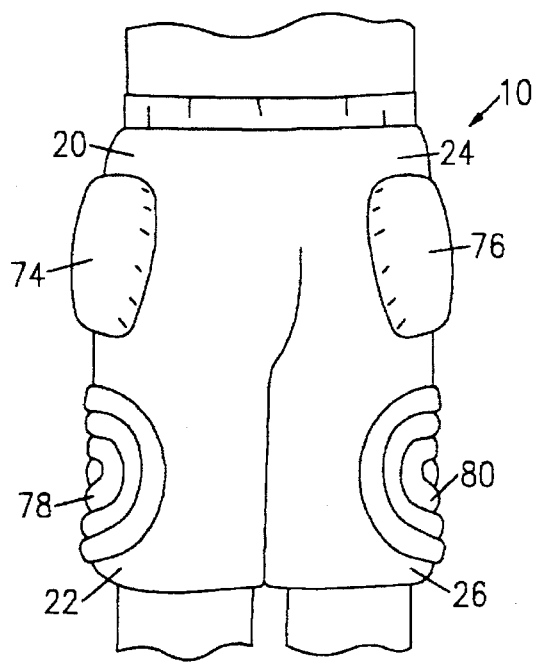
FIG. 4 is a front perspective view of a protective garment according to one embodiment of the present invention.
Figure 5:
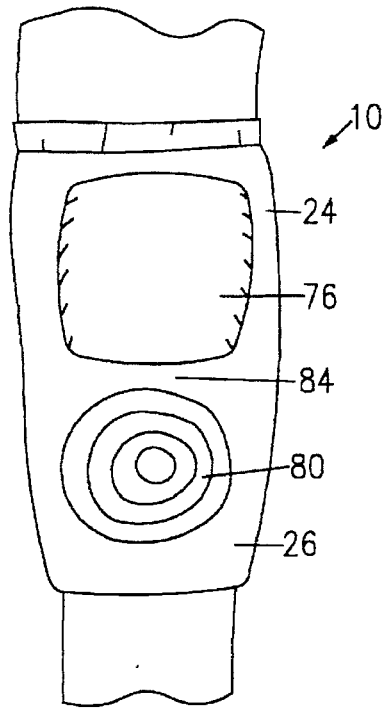
FIG. 5 is a left lateral view of the garment shown in FIG. 4.
Figure 6:
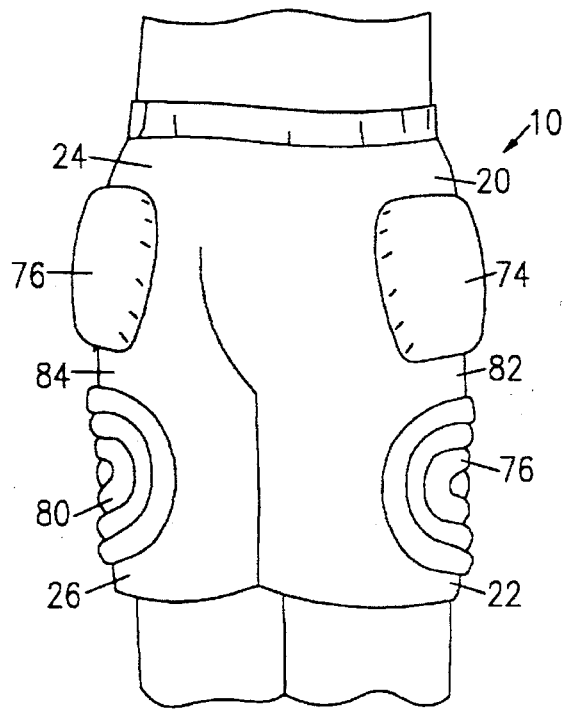
FIG. 6 is a back perspective view of the garment shown in FIG. 4.

Referring now to FIGS. 4–6, there are illustrated a front perspective view, left lateral view and back perspective view, respectively, of a protective garment 10 according to one embodiment of the present invention showing exemplary locations and configurations of protective padding. As can be seen, there is padding in combination with the upper right lateral section 20, the upper left lateral section 24, the lower right lateral section 22 and the lower left lateral section 26. The padding 74 in combination with the upper right lateral section 20 and the padding 76 in combination with the upper left lateral section 24 is non-compartmentalized and roughly rectangular in configuration. The padding 78 in combination with the lower right lateral section 22 and the padding 80 in combination with the lower left lateral section 26 is compartmentalized, being separated into a series of roughly circular concentrically compartments.

The padding 74 in combination with the upper right lateral section 20 is separated from the padding 78 in combination with the lower right lateral section 22 by a first gap 82 of substantially unpadded material. Similarly, the padding 76 in the upper left lateral section 24 is separated from the padding 80 in the lower left lateral section 26 by a second gap 84 of substantially unpadded material. These gaps 82 and 84 are particularly advantageous in that the garment 10 can flex substantially unhindered at the gaps 82 and 84 during flexion and abduction of the thigh, therefore increasing acceptance of the garment 10 for long-term wear.

Further, by limiting the amount and location of the padding to sections over and adjacent to the hip, the garment 10 is made lighter and less bulky than garments designed for other purposes. This also advantageously increases the acceptance of the garment 10 for long-term wear.

Referring now to FIGS. 7–10, there are illustrated exemplary felt lateral views of protective garments, according to embodiments of the present invention, which have padding in various configurations. The right lateral sections, not shown, have padding in similar configurations to that shown in FIGS. 7–10 in each embodiment.

Figure 7:
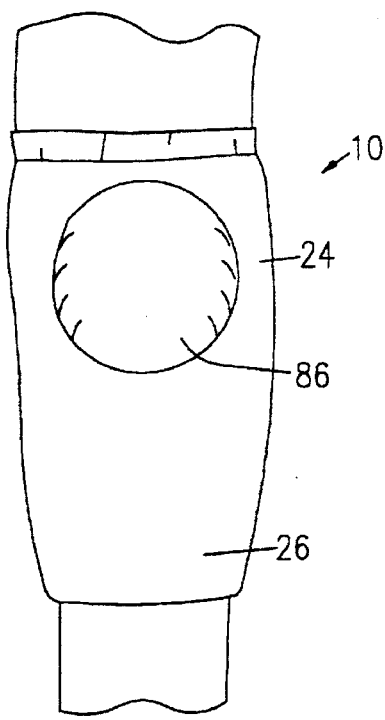
FIG. 7 is a left lateral view of a protective garment according to one embodiment of the present invention showing an exemplary location and configuration of protective padding.

FIG. 7 illustrates a protective garment 10 according to the present invention which has padding 86 in combination with the upper left lateral section 24 that is noncompartmentalized and roughly circular in configuration.

Figure 8:
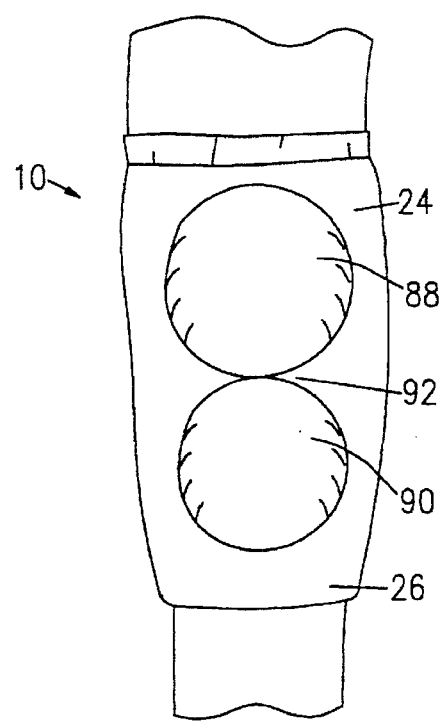
FIG. 8 is a left lateral view of a protective garment according to one embodiment of the present invention showing an exemplary location and configuration of protective padding.

FIG. 8 illustrates a protective garment 10 according to the present invention which has padding 88 in combination with the upper left lateral section 24 that is noncompartmentalized and roughly circular in configuration and padding 90 in combination with the tower left lateral section 26 that is noncompartmentalized and roughly circular in configuration. As can be seen, the padding 88 in combination with the upper left lateral section 24 is separated from the padding 90 in combination with the lower left section by a gap 92. Because the padding 88 and 90 is shown in a substantially circular configuration, the gap 92 is substantially hourglass-shaped.

Figure 9:
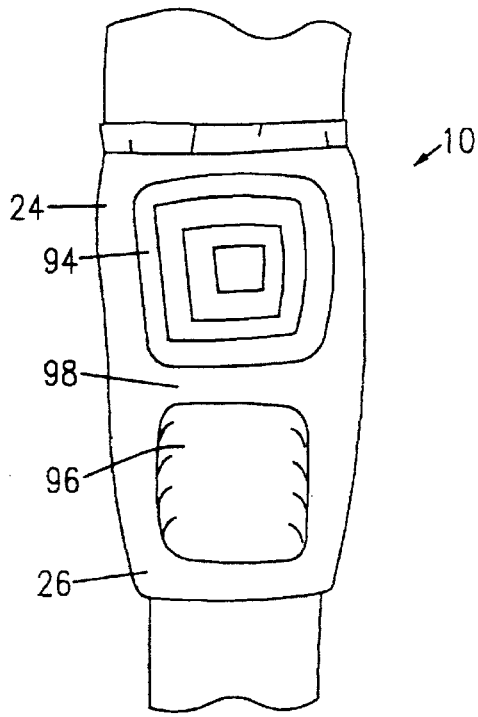
FIG. 9 is a left lateral view of a protective garment according to one embodiment of the present invention showing an exemplary location and configuration of protective padding.

FIG. 9 illustrates a protective garment 10 according to the present invention which has padding 94 in combination with the upper left lateral section 24 that is compartmentalized. The padding 94 is separated into a series of roughly rectangular concentric compartments. Further, the garment 10 has padding 96 in combination with the lower left lateral section 26 that is noncompartmentalized and roughly rectangular in configuration. As can be seen, the padding 94 in combination with the upper left lateral section 24 is separated from the padding 96 in combination with the lower left lateral section 26 by a gap 98. Because the padding 94 and 96 has a substantially rectangular configuration, the gap 98 has substantially parallel sides.

Figure 10:
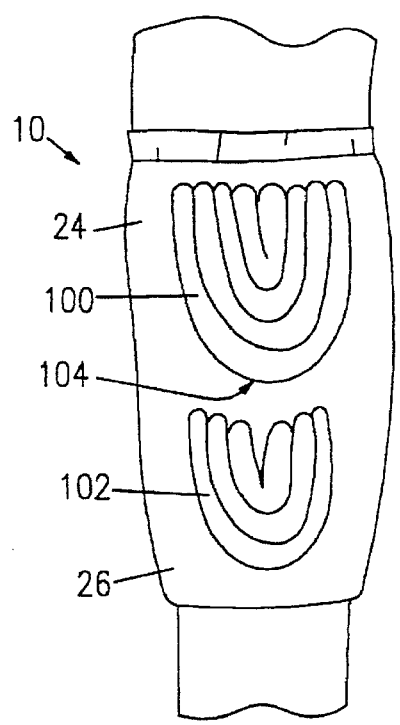
FIG. 10 is a left lateral view of a protective garment according to one embodiment of the present invention showing an exemplary location and configuration of protective padding.

FIG. 10 illustrates a protective garment 10 according to the present invention which has padding 100 in combination with the upper left lateral section 24 that is compartmentalized into a series of U-shaped concentrically oriented compartments. Further, the garment 10 has padding 102 in combination with the lower left lateral section 26 that is compartmentalized into a series of U-shaped concentrically oriented compartments. As can be seen, the padding 100 is separated from the padding 102 by a gap 104. Because of the U-shaped configurations of the padding 100 and 102, the gap 104 has roughly a "V" shape.

Besides the configurations illustrated herein, it will be understood by those with skill in the art with reference to the disclosure herein that other configurations for the padding are suitable for the purposes disclosed. The gap between the padding in combination with the upper lateral and the padding in combination with the lower lateral sections will take on a shape that is dependent upon the configuration of the padding.

Further, it is contemplated within the scope of the present invention that the configuration of padding in combination with the upper right lateral section 20 can be different than the configuration of the padding in combination with the upper left lateral section 24. Further, the configuration of padding in combination with the upper right lateral section 20 can be different than the configuration of the padding in combination with the lower right lateral section 22. And still further, the configuration of padding in combination with the upper left lateral section 24 can be different than the configuration of the padding in combination with the lower left lateral section 26. Combinations of various configurations are, therefore, limited only by the configuration's suitability for the purpose disclosed herein.

In addition to the padding described above, padding can optionally be present in the lower back section 34. This padding is particularly useful in the area overlying the ischial tuberosities because of the tendency of the elderly to lose natural padding in that area and to, thereby, be susceptible to skin breakdown in that area. Aside from making the garment 10 more comfortable to wear, this padding in the lower back section 34 assists in the prevention of decubitus ulcers in this area for those susceptible to such ulcers. When present, padding in the lower back section 34 can take on any of the variety of configurations for padding in combination with other sections as described herein. Further the padding in the lower back can be an extension of padding in the upper right lateral section 20, upper left lateral section 24 or both.

Figure 11:
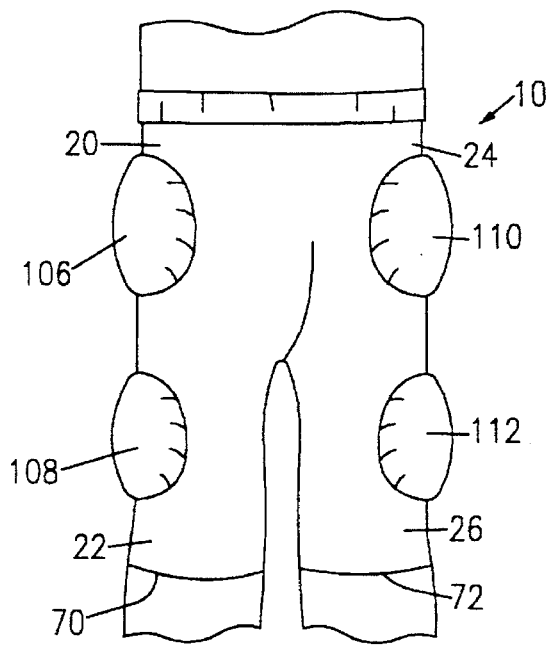
FIG. 11 is a front perspective view of a protective garment according to one embodiment of the present invention.
Figure 12:
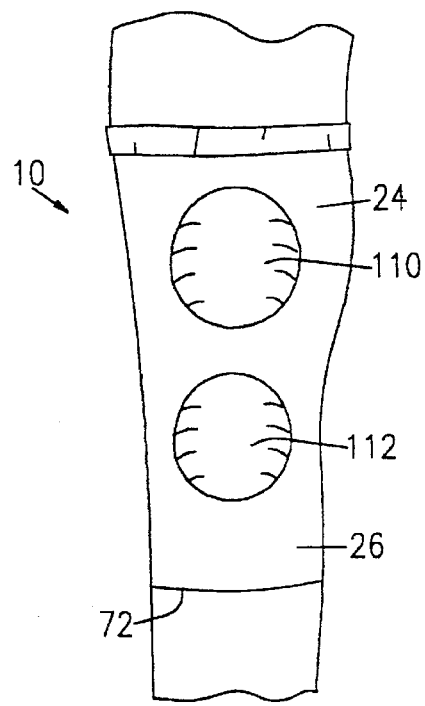
FIG. 12 is a left lateral view of the garment shown in FIG. 11.
Figure 13:
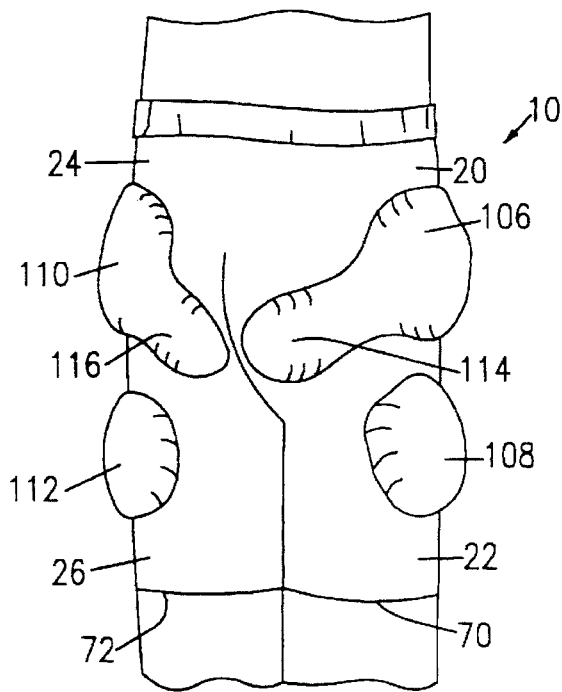
FIG. 13 is a back perspective view of the garment shown in FIG. 11.

Referring now to FIGS. 11–13, there are illustrated a front perspective view, left lateral view and back perspective view, respectively, of a protective garment 10 according to another embodiment of the present invention. The garment 10 comprises a pair of shorts that are substantially form-fitting, having a waist opening 68, a right leg opening 70, a left leg opening 70 and, optionally, a waistband 12.

The garment 10 can comprise any of a variety of natural or synthetic materials, such as cotton, or a blend of natural or synthetic materials, as would be understood by those with skill in the art with reference to the disclosure herein.

Preferably, the material comprises an elastic fabric to render the garment 10 comfortably form-fitting. Further, the garment 10 is preferably light-weight, washable, and substantially permeable to water vapor so that moisture can evaporate from the skin therethrough. The light-weight and permeability advantageously increases the acceptability of the garment 10 for long-term wear.

As can be seen in FIGS. 11–13, the form fitting garment 10 according to one embodiment of the present invention includes padding 106 in combination with the upper right lateral section 20, padding 108 in combination with the lower right lateral section 22, padding 110 in combination with the upper left lateral section 24 and padding 112 in combination with the lower left lateral section 26. The configurations and location of padding can be as disclosed herein for the embodiments of the garment 10 which are loose fitting. For exemplary purposes only, the padding 106 in combination with the upper right lateral section 20, the padding 108 in combination with the lower right lateral section 22, the padding 110 in combination with the upper left lateral section 24 and the padding 112 in combination with the lower left lateral section 26 is shown as being in a noncompartmentalized circular configuration.

Further, as illustrated in FIG. 13, the embodiment has padding 114 and 116 in combination with the lower back section 34 overlying the area corresponding to the ischial tuberosities. The padding 114 in the lower back section 34 is an extension of the padding 106 in combination with the upper right lateral section 20 and the padding 116 in the lower back section 34 is an extension of the padding 110 in combination with the upper left lateral section 24.

In addition to the features described above, the protective garment 10 according to the present invention can further comprise a fly in the front section 18 for permitting urination therethrough. Also, the garment 10 can comprise absorbent material in one or more of the front section 18, the lower right medial section 28, the lower left medial section 30, and the lower back section 34 to assist in prevention of leakage due to incontinency.

In use, the protective garment 10 according to the present invention is put on as one would ordinarily put on underwear intended for the lower portion of the body. If the padding in combination with the various sections is separable from the remainder of the garment 10, then the padding is combined with the sections at such time as protection is desired from injuries to the hip during a fall. If the padding in combination with various sections of the garment 10 is not separable, then the garment 10 assists in protecting the hip during the entire time that it is worn.

Although the present invention has been described in considerable detail with reference to certain preferred embodiment, other embodiments are possible. For example, the protective garment described above can be incorporated into a larger garment covering the torso, torso and upper extremities or lower portions of the lower extremities, or a combination of the foregoing. Therefore, the spirit and scope of the appended claims should not be limited to the description of the preferred versions herein.

I claim:

1. A protective garment for a hip joint and hip of a person, comprising: a pair of shorts extending from a waist opening superiorly to two leg openings inferiorly; the garment having a front section anteriorly, an upper right lateral section rightward laterally adjacent to the front section, a lower right lateral section inferiorly adjacent to the upper right lateral section, an upper left lateral section leftward laterally adjacent to the front section, a lower left lateral section inferiorly adjacent to the upper left lateral section, a lower right medial section medially adjacent the lower right lateral section and inferiorly adjacent the front section, a lower left medial section medially adjacent the lower left lateral section and inferiorly adjacent the front section, an upper back section posteriorly adjacent and between the upper right lateral and upper left lateral sections and a lower back section inferiorly adjacent the upper back section and posteriorly adjacent and between the upper right lateral and upper left lateral sections; the garment further having protective padding suitable for absorbing or dispersing energy transmitted to the hip during a fall, the padding being in combination with the upper right lateral section, the lower right lateral section, the upper left lateral section and the lower left lateral section; wherein the padding in combination with the upper right lateral section is separated from the padding in combination with the lower right lateral section by a first gap, wherein the padding in combination with the upper left lateral section is separated from the padding in combination with the lower left lateral section by a second gap wherein the padding is substantially, solely configured to cover a proximal portion of a femur and a lateral portion of a ischium and ilium of the person the first and second gaps comprising substantially unpadded flexible material, the gaps allowing substantially unhindered flexion and abduction of the hip joint; wherein the padding in combination with the lower right lateral section extends posteriorly beyond a line approximately bisecting the right lateral side of the garment anteriorly and posteriorly; and wherein the front section, upper back section, lower right medial section and lower left medial section are substantially devoid of protective padding.

2. The protective garment of claim 1, further comprising protective padding in combination with the lower back section.

3. The protective garment of claim 1, wherein the padding in at least one section is compartmentalized.

4. The protective garment of claim 1, wherein the padding in at least one section is noncompartmentalized.

5. The protective garment of claim 1, wherein the padding in at least one section is compartmentalized and in at least one other section is noncompartmentalized.

6. The protective garment of claim 1, wherein the padding in at least one section is configured in a pattern selected from the group consisting of a series of diagonally oriented compartments, a series of circularly concentric oriented compartments, a series of ovally concentric oriented compartments, a series of triangularly concentric oriented compartments, a series of rectangularly concentric oriented compartments, a series of U-shaped concentrically oriented compartments, a series of waffle-like compartments and a combination of the foregoing.

7. The protective garment of claim 1, wherein the shorts are substantially loose fitting.

8. The protective garment of claim 1, wherein the shorts are substantially form fitting.

9. The protective garment of claim 1, further comprising absorbent material in combination with at least one of the front section, the lower right medial section, the lower left medial section, the lower back section or a combination of the foregoing sections.

10. The protective garment of claim 1, wherein the garment is substantially permeable to water vapor.

11. The protective garment of claim 1, wherein the front section comprises a fly for permitting urination therethrough.

12. A method of protecting the hip of a person comprising the step of: placing the person's legs through the two leg openings of the garment according to claim 1, such that the protective padding is adjacent the person's hip region.

* * * * *